US007547424B2

(12) United States Patent
Haab et al.

(10) Patent No.: US 7,547,424 B2
(45) Date of Patent: Jun. 16, 2009

(54) METHOD AND APPARATUS FOR MAKING PARTITIONED SLIDES

(75) Inventors: Brian Brummeler Haab, Jenison, MI (US); David Kruithoff, Vancouver, WA (US)

(73) Assignee: Van Andel Research Institute, Grand Rapids, MI (US)

( * ) Notice: Subject to any disclaimer, the term of this patent is extended or adjusted under 35 U.S.C. 154(b) by 614 days.

(21) Appl. No.: 11/228,588

(22) Filed: Sep. 16, 2005

(65) Prior Publication Data

US 2006/0062695 A1 Mar. 23, 2006

Related U.S. Application Data

(60) Provisional application No. 60/611,585, filed on Sep. 21, 2004.

(51) Int. Cl.
*A61L 2/04* (2006.01)

(52) U.S. Cl. ........................... 422/307; 422/99; 101/41; 101/129; 427/2.11; 118/243

(58) Field of Classification Search ................. 422/100, 422/102; 101/41, 129; 427/2.11, 282, 256; 118/202, 243
See application file for complete search history.

(56) References Cited

U.S. PATENT DOCUMENTS 1,654,369 A 12/1927 George
3,432,275 A 3/1969 Unger
3,447,863 A 6/1969 Patterson
3,579,540 A 5/1971 Ohlhausen
3,777,283 A 12/1973 Elkins
3,961,346 A 6/1976 White
4,011,350 A 3/1977 Markovits et al.
4,022,521 A 5/1977 Hall et al.
4,183,614 A 1/1980 Feldman
4,220,273 A 9/1980 Faulkner
4,299,441 A 11/1981 Parker
4,387,972 A 6/1983 Valencia
4,447,140 A 5/1984 Campbell et al.
4,505,557 A 3/1985 Golias
4,722,598 A 2/1988 Ford (Continued)

FOREIGN PATENT DOCUMENTS

GB 1528918 10/1978

(Continued)

OTHER PUBLICATIONS

"Polysiloxanes" by Norman R. Mowrer, Ameron International Performance Coatings and Finishes, Nov. 2003.*

(Continued)

*Primary Examiner*—Jill Warden
*Assistant Examiner*—Anita B Damron
(74) *Attorney, Agent, or Firm*—Price, Heneveld, Cooper, DeWitt & Litton, LLP

(57) ABSTRACT

An apparatus for placing a hydrophobic barrier on an examination slide including a vessel, a printer block having a printing surface to form a hydrophobic barrier on the examination slide in a specified pattern, a slide holder, and a reversible actuator. The invention also includes a method for placing a hydrophobic barrier on an examination slide in a specified pattern.

22 Claims, 4 Drawing Sheets

U.S. PATENT DOCUMENTS

| | | | | |
|---|---|---|---|---|
| RE33,826 | E | 2/1992 | Mitchell | |
| 5,766,677 | A | 6/1998 | Dimou et al. | |
| 5,770,441 | A | 6/1998 | Lipton | |
| 5,948,685 | A | 9/1999 | Angros | |
| 6,103,479 | A | 8/2000 | Taylor | |
| 6,235,541 | B1 | 5/2001 | Brizzolara | |
| 6,390,697 | B1 * | 5/2002 | O'Mera et al. | 400/120.16 |
| 6,396,995 | B1 | 5/2002 | Stuelpnagel et al. | |
| 6,407,042 | B1 | 6/2002 | Ward et al. | |
| 6,555,384 | B1 | 4/2003 | Angros | |
| 6,645,434 | B1 | 11/2003 | Muramatsu et al. | |
| 6,673,620 | B1 | 1/2004 | Loeffler et al. | |
| 6,713,304 | B2 | 3/2004 | Angros | |
| 2002/0102186 | A1 | 8/2002 | McEntee et al. | |
| 2002/0151040 | A1 | 10/2002 | O'Keefe et al. | |
| 2003/0003586 | A1 * | 1/2003 | Angros | 436/63 |
| 2003/0068253 | A1 | 4/2003 | Bass et al. | |
| 2003/0109059 | A1 | 6/2003 | Adrien et al. | |
| 2003/0119028 | A1 | 6/2003 | Graves et al. | |
| 2003/0215806 | A1 | 11/2003 | Lewis | |
| 2003/0231987 | A1 | 12/2003 | Carmack et al. | |
| 2004/0082058 | A1 | 4/2004 | Schleifer et al. | |
| 2005/0233337 | A1 * | 10/2005 | Peck et al. | 435/6 |

FOREIGN PATENT DOCUMENTS

| | | | |
|---|---|---|---|
| WO | WO 00/71992 | A1 | 11/2000 |

OTHER PUBLICATIONS

M-Tech Diagnositics, LTD, "http://www.m-techdiagnostics.ltd.uk/aquahold.shtml," Apr. 26, 2004 (4 pages).

RPI Corporation, "http://www.rpicorp.com/index.php?cat=46," Apr. 26, 2004 (6 pages).

Grace Bio Labs, "http://www.gracebio.com/ProPlate.htm," Apr. 26, 2004 (8 pages).

Grace Bio Labs, "http://www.gracebio.com/prodpress.html," Apr. 26, 2004 (2 pages).

Grace Bio Labs, "http://gracebio.com/prodsecursealhy.html," Apr. 26, 2004 (2 pages).

Grace Bio Labs, "http://gracebio.com/prodfastwells.html," Apr. 26, 2004 (2 pages).

Grace Bio Labs, "http://www.gracebio.com/prodcovperf.html," Apr. 26, 2004, (2 pages).

Fox et al., "A simple and inexpensive culture device for cell growth, quantitative microscopy and autoradiography," Journal of Microscopy, vol. 112 (No. 2), p. 239-242.

Dobies et al., "Application of the paraffin ring method for preparation of temporary mounts with nematodes," Journal of Plant Protection Research, vol. 41 (No. 3), p. 312-314.

Jackman et al., "Using elastomeric membranes as dry resist and for dry lift-off," Langmuir, vol. 15 (No. 8), p. 2973-2974.

Xia et al., "Complex optical surfaces formed by replica molding against elastomeric masters," Science, vol. 273 (No. 5273), p. 347-349.

Zhu et al., "Analysis of yeast protein kinases using protein chips," Nature Genetics, vol. 26 (No. 3), p. 283-289.

Graham et al., "Novel fixation of plant tissue, straining through paraffin with Alcian Blue and hematoxylin, and improved slide preparation," Biotechnic & Histochemistry, vol. 70 (No. 5), p. 263-266.

Colloff, "A new and rapid method of making permanent preparations of large numbers of house-dust mites for light microscopy," Experimental & Applied Acarology, vol. 7, p. 323-326.

Voegtlin, "A method for making customized, thick labels for microscope slides," The Great Lakes Entomologist, vol. 32 (No. 4), p. 293-298.

Leif et al., "Optimization of the binding of dissociated exfoliated cervico vaginal cells to glass microscope slides," The Journal of Histochemistry and Cytochemistry, vol. 25 (No. 7), p. 538-543.

Cundell et al., "A rapid method for detection of coliform bacteria," Dev. Ind. Microbiol., vol. 20, p. 571-577.

M-Tech Diagnositics LTD, "http://www.m-techdiagnostics.ltd.uk/aquahold.shtml," Apr. 26, 2004 (4 pages),"AquaHold Pap Pen".

"Hybridization" RPI Corporation, "http://www.rpicorp.com/index.php?cat=46," Apr. 26, 2004 (6 pages).

"ProPlate TM Multiarray Slide System" Grace Bio Labs, "http://www.gracebio.com/ProPlate.htm," Apr. 26, 2004 (8 pages).

"Press-to-Seal Silicone Isolators" Grace Bio Labs, "http://www.gracebio.com/prodpress.html," Apr. 26, 2004 (2 pages).

"SecureSeaal 198 Hybridization Chambers" Grace Bio Labs, "http://gracebio.com/prodsecursealhy.html," Apr. 26, 2004 (2 pages).

"Fastwells" Grace Bio Labs, "http://gracebio.com/prodfastwells.html," Apr. 26, 2004 (2 pages).

"CoverWell 198 Perfusion Chambers" Grace Bio Labs, "http://www.gracebio.com/prodcovperf.html," Apr. 26, 2004 (2 pages).

* cited by examiner

METHOD AND APPARATUS FOR MAKING PARTITIONED SLIDES

CROSS-REFERENCE TO RELATED APPLICATIONS

This application claims benefit of provisional application Ser. No. 60/611,585, filed Sep. 21, 2004, entitled METHOD AND APPARATUS FOR MAKING PARTITIONED SLIDES, the entire contents of which are incorporated herein in their entirety.

FIELD OF THE INVENTION

This invention relates to methods and apparatus for partitioning examination slides.

BACKGROUND OF THE INVENTION

Microarray technology is known to be useful in monitoring levels of gene expression. Microarrays include regions of either different polynucleotides or antibodies arranged in a predetermined configuration and bound on a substrate. These regions are positioned at specific locations on the substrate. In a typical experiment, a sample of total RNA, mRNA, or proteins are collected from two individuals or under two treatment conditions. In use, when exposed to a sample from an individual or a under a specific treatment condition, the array will exhibit an observed binding pattern of the cDNA (mRNAs reverse transcribed) or proteins to the bound DNA or antibodies, respectively. A basic principle of the microarray is the differential labeling of two samples (e.g., by radiolabeling or fluorescent dyes) and observing the intensities of each sample at each location in the microarray. Using this technique, an investigator can determine whether specific genes are upregulated or downregulated in various individuals and under various treatment conditions. By using a single reference sample as a control for a series of experimental samples, the investigator can compare relative levels of expression among the treatment samples.

In one format, microarray analysis is conducted on an examination slide, such as microscope slide or a diagnostic plate. Such examination slides generally are made from clear glass or plastic, but may be made of other materials. For higher throughput studies, an investigator will conduct several microarray assays on a single microscope slide. Under such circumstances, however, with ordinary manipulation and processing of the slide during the microarray process, liquid from one sample on the slide may spill over or migrate, and mix with another sample on the slide. Accordingly, various barriers have been developed to prevent contamination between multiple samples on a microarray slide. Known products for separating samples on a slide include rubber gaskets, with or without adhesive, hydrophobic markers known as PAP pens, and manufactured barriers such as Teflon®. There are problems with these products, however: gaskets without adhesive do not seal well; when gasket adhesive is used, it can be dissolved by solvents and interfere with experiments; hydrophobic pens are tedious, difficult to use accurately, and dissolve in certain detergents and solvents; and manufactured barriers are expensive and inflexible. Also, gaskets need to be removed before scanning in a typical laser scanner (and some slide coatings will peel off when the gasket is removed). Microarray scanners commonly have clearance for the slide and sample of approximately 250 micrometers.

SUMMARY OF THE INVENTION

These and other features, advantages, and objects of the present invention will be further understood and appreciated by those skilled in the art by reference to the following specification, claims and appended drawings.

In one embodiment, the present invention is an apparatus for placing a hydrophobic barrier on an examination slide. The apparatus includes: a vessel and a printer block having a printing surface configured to carry hydrophobic liquid to form a hydrophobic barrier on the examination slide in a specified pattern, wherein the printer block is moveable between a first position in which the printing surface is in the hydrophobic liquid in the vessel, and a second position in which the printing surface is out of the vessel. The apparatus of the invention also includes a slide holder for holding the examination slide adjacent to the printing surface when the printer block is in the second position, and a reversible actuator for moving the printer block between the first position and the second position. Because some hydrophobic liquids are in solid phase at room temperature, in one embodiment, a heater is provided to maintain the hydrophobic liquid in liquid phase during application of the hydrophobic barrier to the examination slide.

In another embodiment, the present invention is a method for making an examination slide having defined sample areas, including the steps of: (a) obtaining an examination slide, a hydrophobic liquid, and an apparatus for placing hydrophobic liquid on the examination slide to define sample areas, the apparatus having a vessel for the hydrophobic liquid, a printer block having a printing surface formed in a specified pattern, wherein the printer block is moveable between a first position with the printing surface of the printer block in the hydrophobic liquid and a second position in which the printing surface is out of the vessel, a slide holder for holding the examination slide adjacent to the printing surface when the printing block is in the second position, and a reversible actuator for moving the printer block between the first position and the second position; (b) placing the hydrophobic liquid in the vessel and the printer block in the first position; (c) placing the examination slide in the slide holder; (d) engaging the actuator to move the printer block from the first position to the second position, thus carrying the hydrophobic liquid on the printing surface of the printer block and transferring the hydrophobic liquid from the printing surface to the examination slide in the specified pattern; and (e) removing the examination slide from the slide holder. If the hydrophobic liquid used by the investigator is in solid phase at room temperature, the apparatus also includes a heater, and the method includes obtaining a heater for use with the apparatus and applying heat to the vessel to convert the hydrophobic liquid from a solid to a liquid phase.

DETAILED DESCRIPTION OF THE PREFERRED EMBODIMENTS

The present invention may be understood more readily by reference to the following detailed description of specific embodiments set forth hereinafter.

As used in the application: "a" can mean one or more, depending on the context with which it is used; the term "oligonucleotide" refers to primers, probes, and oligomer fragments; the term "antibody" refers to monoclonal and polyclonal antibodies; the term "liquid" refers to a liquid material or a liquid biological sample (e.g., blood, urine, plasma, or other bodily fluids) which material is in liquid phase at room temperature or can be maintained in liquid phase by the application of heat; the term "hydrophobic" refers to water resistant or water repellent; the term "examination slide" refers to any type of planar diagnostic plate used in microscopic or diagnostic analysis and can have any shape suitable for use in analytic devices.

Figure 1:
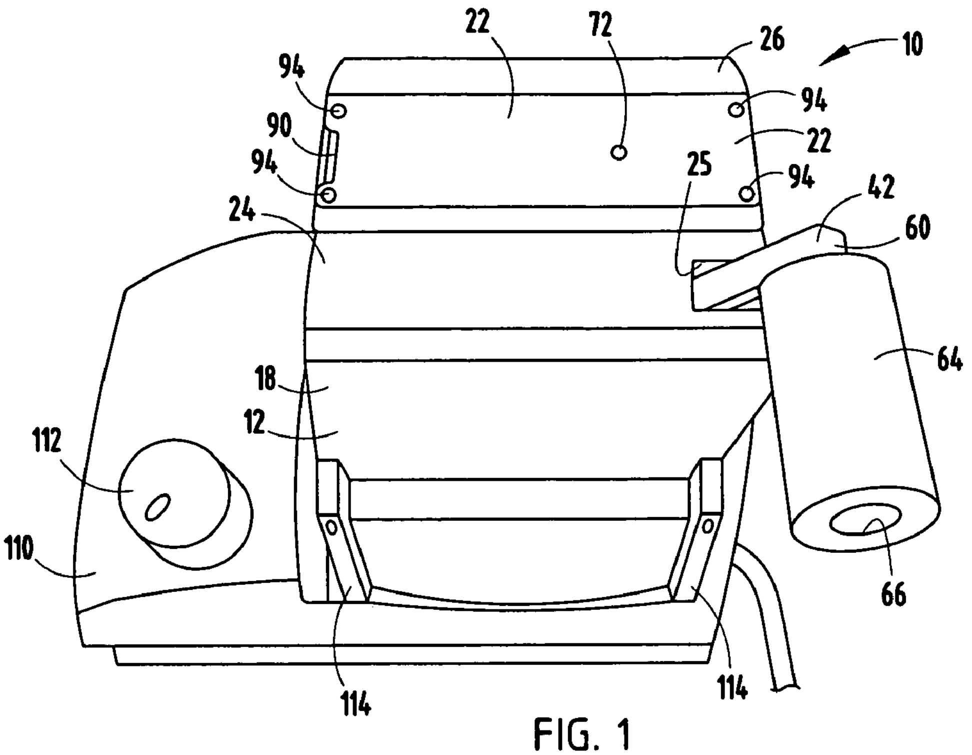
FIG. 1 is a side perspective view of the apparatus of the present invention.
Figure 6:
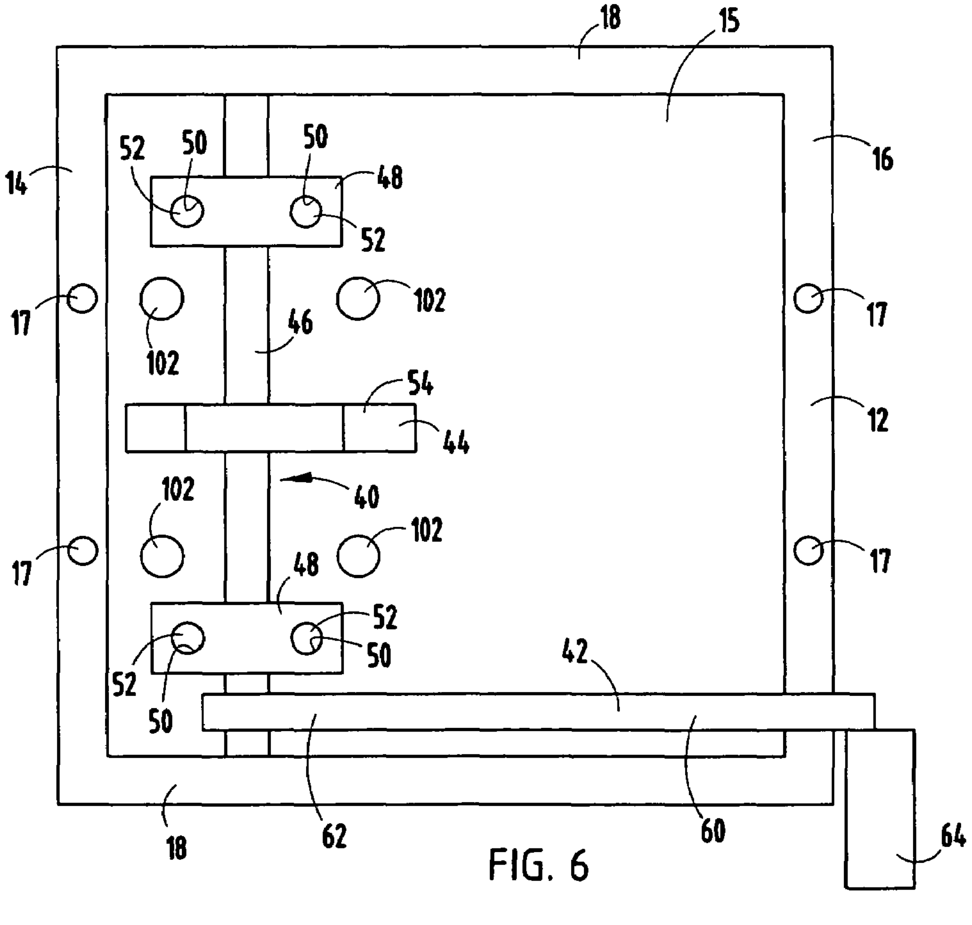
FIG. 6 is a top plan view of the apparatus of the present invention in which the slide holder, right and left top covers, and printer block are not shown.

FIG. 1 shows the apparatus of the present invention having the general reference numeral 10. Apparatus 10 includes a vessel 12, having a front vessel wall 14, a rear vessel wall 16, and two opposing side vessel walls 18 (FIG. 6). Front vessel wall 14 and rear vessel wall 16 include vessel wall apertures 17 (FIG. 6). As shown in FIGS. 1-3 and 6, vessel 12 is configured to contain a hydrophobic liquid 20. Vessel 12 is covered by a centrally located slide holder 22, and by a removable right vessel cover 24 and a removable left vessel cover 26 (FIG. 1). Right vessel cover 24 includes a cover slot 25. Vessel covers 24 and 26 are removable to allow for loading of hydrophobic liquid 20 into vessel 12. When heat is applied to vessel 12 as described herein and, consequently, to hydrophobic liquid 20, slide holder 22 and vessel covers 24 and 26 help to prevent the escape of heat from vessel 12 and from hydrophobic liquid 20.

Figure 2:
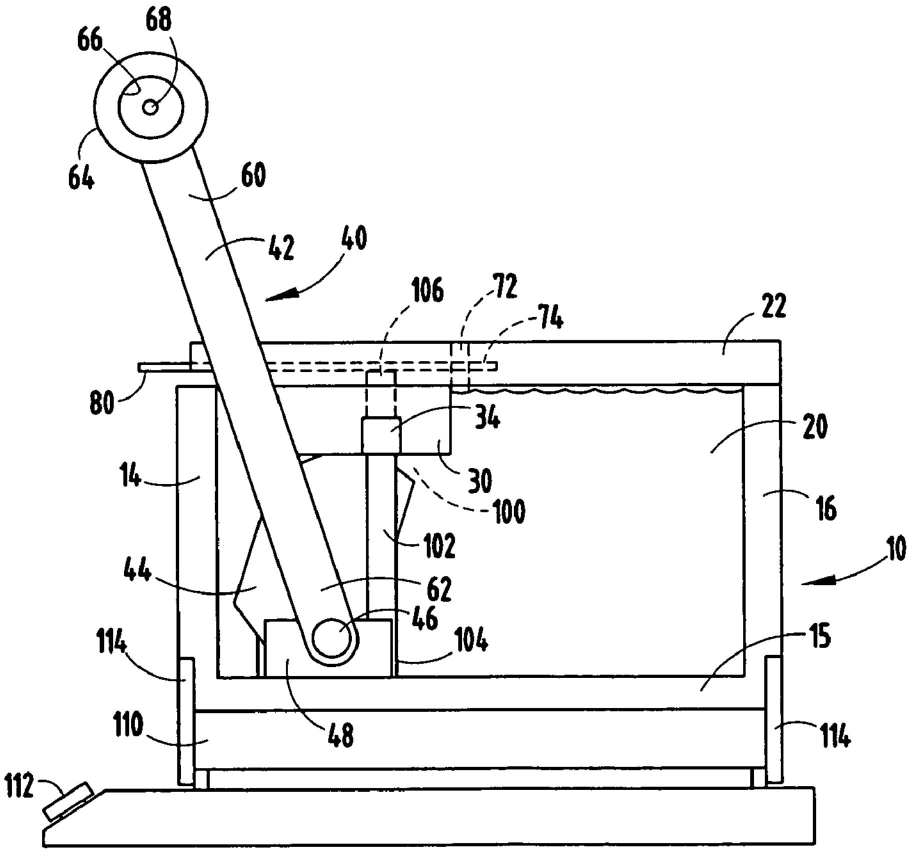
FIG. 2 is a side view of the apparatus of the present invention viewed along line II-II of FIG. 5 with the printer block shown in a second position.
Figure 3:
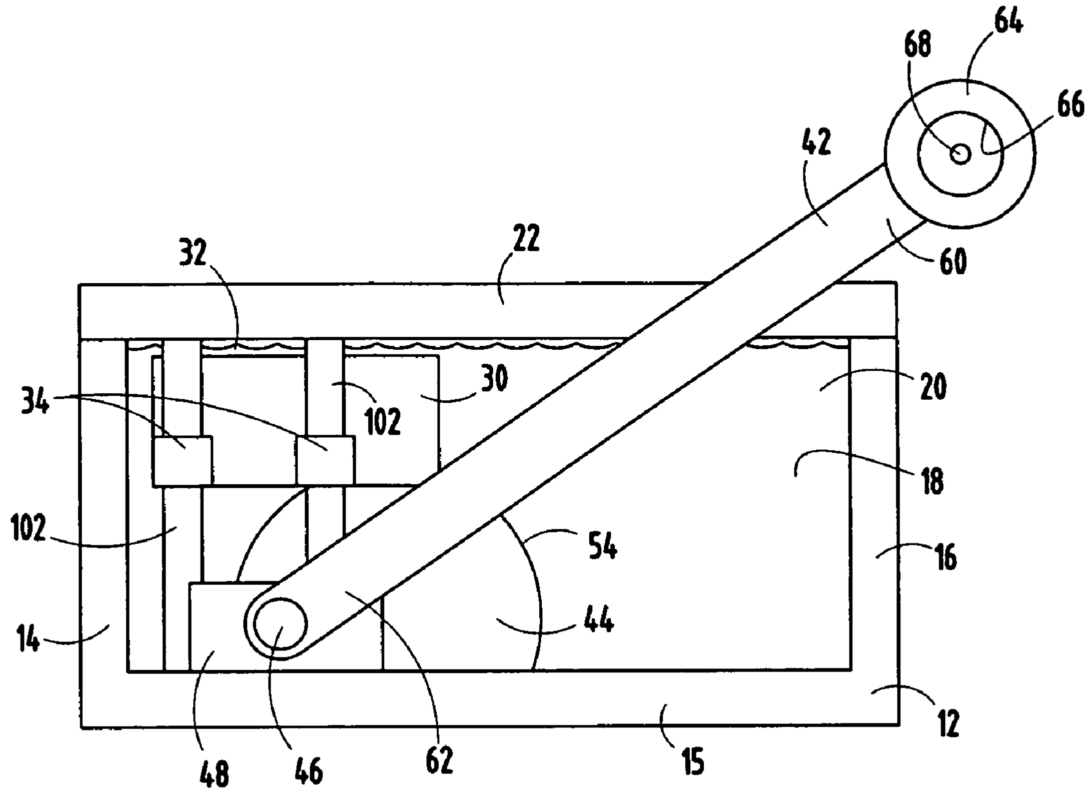
FIG. 3 is a side view of the apparatus of the present invention viewed along line II-II of FIG. 5 with the printer block shown in a first position.
Figure 5:
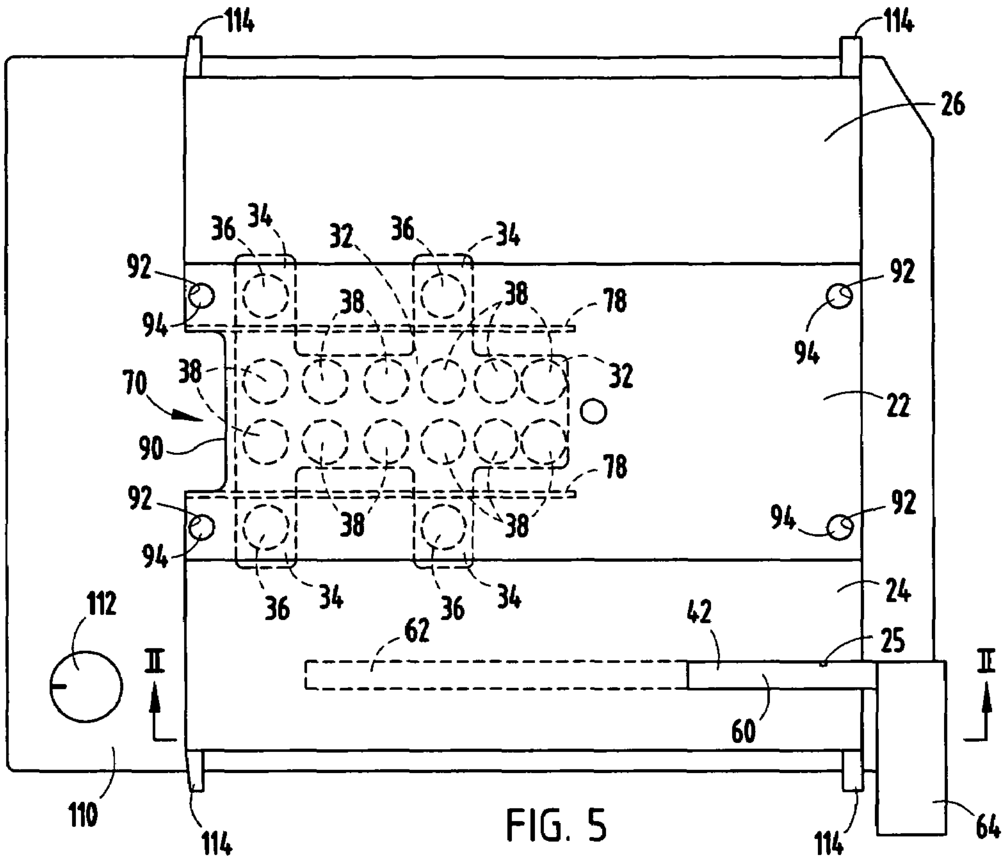
FIG. 5 is a top plan view of the apparatus of the present invention showing the printer block, step channels, and a portion of the lever arm in dashed lines.

Referring to FIGS. 2, 3, and 5, apparatus 10 includes a printer block 30 having a printing surface 32. Printer block 30 also includes four flanges 34 each extending outwardly from printer block 30, and each flange 34 incorporating a flange aperture 36. Additionally, printer block 30 includes printer block apertures 38 through printer block 30, which printer block apertures 38 allow hydrophobic liquid 20 to flow through printer block 30.

Printer block 30 is moveable by a reversible actuator 40 from a first position (FIG. 3) to a second position (FIG. 2). Actuator 40 includes a lever arm 42, a pivot member 44, an axel 46, and pivot collars 48 (FIGS. 2, 3, and 6). Vessel 12 also includes a bottom 15 connected to vessel walls 14, 16, and 18 of vessel 12. Pivot collars 48 include pivot collar apertures 50, and pivot collars 48 are attached to vessel bottom 15 by pivot collar bolts 52 through pivot collar apertures 50 and into vessel bottom 15. Axel 46 extends between vessel side walls 18 and is rotationally mounted within pivot collars 48.

Lever arm 42 has a top end 60 and a bottom end 62, and also includes a handle 64. Handle 64 has an aperture 66 and handle 64 is attached to top end 60 of lever arm 42 by a handle bolt 68. Cover slot 25 of right vessel cover 24 allows lever arm 42 to extend out of vessel 12 (FIG. 1).

Both lever arm 42 and pivot member 44 are fixedly attached to axel 46 such that movement of lever arm 42 moves pivot member 44. As shown in FIGS. 2 and 3, pivot member 44 has a cammed surface 54. Vessel 12 is filled with a sufficient amount of hydrophobic liquid 20 such that printing surface 32 of printer block 30 is covered by hydrophobic liquid 20 (FIGS. 2 and 3). When lever arm 42 of actuator 40 is positioned adjacent rear vessel wall 16, printing surface 32 of printer block 30 is covered by hydrophobic liquid 20. In order to move printer block 30 from the first position (FIG. 3) to the second position (FIG. 2), right vessel cover 24 is removed and lever arm 42 is moved from its position adjacent rear vessel wall 16 (FIG. 3) toward front vessel wall 14 (FIG. 2), causing axel 46 to rotate within pivot collars 48 and causing pivot member 44 to rotate in the same direction as axel 46 and push printer bock 32 away from vessel bottom 15. Due to the contour of cammed surface 54 of pivot member 44, movement of lever arm 42 causes printer block 30 to be moved upwardly in a smooth, regulated manner.

Figure 7:
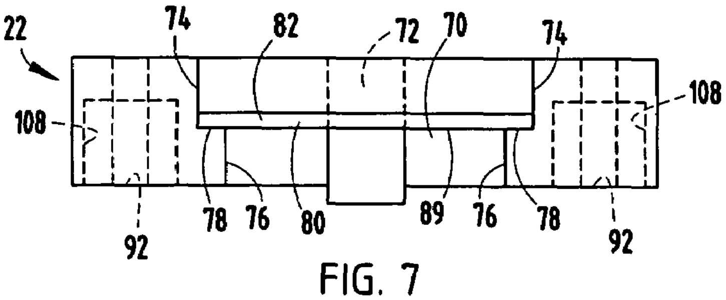
FIG. 7 is a side view of the front end of the slide holder of the present invention.
Figure 8:
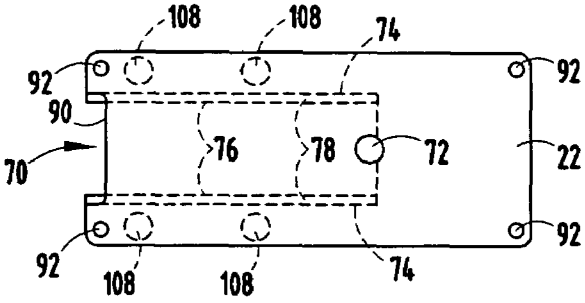
FIG. 8 is a top plan view of the slide holder of the present invention.

Slide holder 22 includes a step channel 70 and a stop 72 (FIGS. 5 and 8). As shown in FIGS. 7 and 8, step channel 70 of slide holder 22 includes: two opposing outer channel walls 74; two opposing inner channel walls 76; and two step channel shelves 78 perpendicular to and extending between outer channel walls 74 and inner channel walls 76 (i.e., channel walls 74 and 76 are the risers and step channel shelves 78 the treads of the stairs formed by these elements). The two outer channel walls 74 are spaced apart from each other sufficiently to accommodate an examination slide 80 (FIGS. 2, 5, 7, and 8). As shown in FIG. 8, slide holder 22 further includes a front end 90, four slide holder apertures 92, and four guidepost detents 108. Slide holder bolts 94 are inserted through slide holder apertures 92 into vessel wall apertures 17 of vessel 12 to attach slide holder 22 to vessel 12 such that front end 90 of slide holder 22 is adjacent front vessel wall 14 of vessel 12 (FIG. 1). Stop 72 of slide holder 22 extends into step channel 70 as shown in FIGS. 2 and 7.

Examination slide 80 (FIG. 8) includes a slide front end 82, a slide rear end 84, two slide side edges 86, a slide top surface 88, and a slide bottom surface 89. When examination slide 80 is fully inserted into front end 90 of slide holder 22, slide bottom surface 89 rests on step channel shelves 78 and rear end 84 of examination slide 80 abuts stop 78 of slide holder 22 (FIG. 7). Thus, when inserted in slide holder 22, examination slide 80 is aligned front-to-back within slide holder 22 by stop 72, and also is aligned side-to-side within slide holder 22 by the two outer channel walls 74 of step channel 70. With slide rear end 84 stopped by stop 72, front end 82 of examination slide 80 projects outwardly from front end 90 of slide holder 22 such that a user can grasp examination slide 80 during insertion and removal of slide 80 from slide holder 22.

Apparatus 10 also includes a guide mechanism 100 to align the printing surface 32 of printer block 30 with the slide holder 22 and the slide top surface 88 of examination slide 80 while printer block 30 is moved from the first position (FIG. 3) to the second position (FIG. 2) by actuator 40. Specifically, guide mechanism 100 includes four guideposts 102 extending vertically upward from vessel bottom 15 of vessel 12, and flange apertures 36 of flanges 34 of printer block 33 (FIGS.

2-5). Guideposts 102 have a first end 104 and second end 106 (FIG. 2). Each of guide posts 102 are attached at the first end 104 with vessel bottom 15 and at the second end 106 in guidepost detents 108 of slide holder 22. Flange apertures 36 are large enough to slideably receive guideposts 102 there through, but the size relationship between flange apertures 36 and guide posts 102 is such that, upon actuation of actuator 40, printer block 32 moves upwardly away from vessel bottom 15 in a direction generally perpendicular to the plane of vessel bottom 15. When actuator 40 is actuated so that printer block 30 moves from the first position (FIG. 3) to the second position (FIG. 2), pivot member 44 rotates to push printer block 30 upwardly guided by guideposts 102. The present invention also contemplates, alternatively, a combination of elements to pull printer block 30 upwardly from vessel bottom 15 in a guided manner (not shown).

Figure 4:
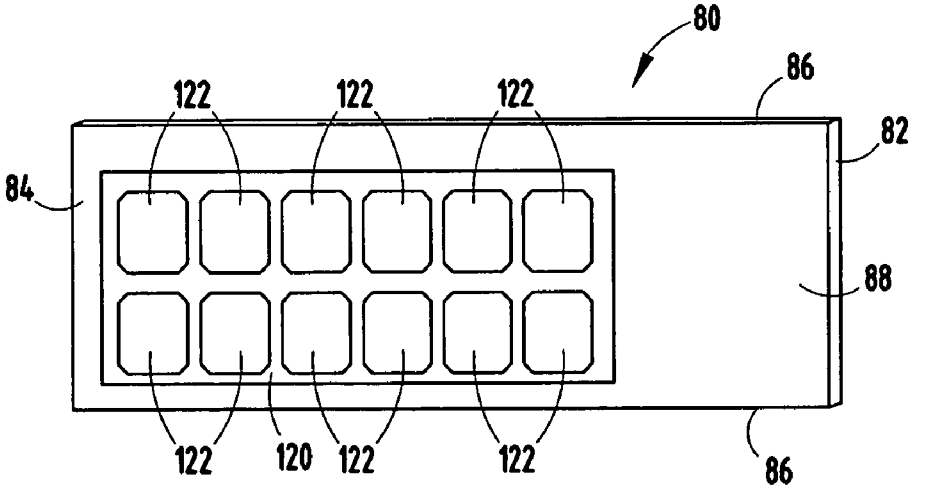
FIG. 4 is a top perspective view of an examination slide made according to the apparatus of the present invention.

Various hydrophobic liquids can be used to fill vessel 12. For example, hydrophobic liquid 20 is wax, paraffin, silicone, or any other polymer that is in solid phase at room temperature but can be liquefied with the application of heat. The hydrophobic liquid selected to create the hydrophobic barrier should be highly resistant to removal by chemicals and physical removal by washing. Such liquids are well known to one of ordinary skill in the art. In a preferred embodiment of the present invention, wax is used as hydrophobic liquid 20. At room temperature, the preferred wax is in a solid phase. Accordingly, apparatus 10 also includes a heater 110 below vessel 12. The heater can be any conventional heat source, such as a hot plate made by Fisher Scientific. As shown in FIGS. 1 and 5, heater 110 has a heater control 112. To operate apparatus 10 and apply a hydrophobic barrier 120 to slide top surface 88 of examination slide 80 (FIG. 4), hydrophobic liquid 20 must be in a liquid phase, and heater 110 is utilized for this purpose. Specifically, heater control 112 is adjusted to convert and maintain hydrophobic liquid 20 in liquid phase. Vessel 12 is attached to heater 110 by four heater brackets 114 (FIGS. 1, 2, and 5). In one embodiment of the invention, the heater control is set to maintain the temperature of the hydrophobic liquid 20, initially, at 550 degrees Centigrade for fifteen minutes, followed by maintenance of the hydrophobic liquid 20 at 180 degrees Centigrade for ten minutes.

Figure 9:
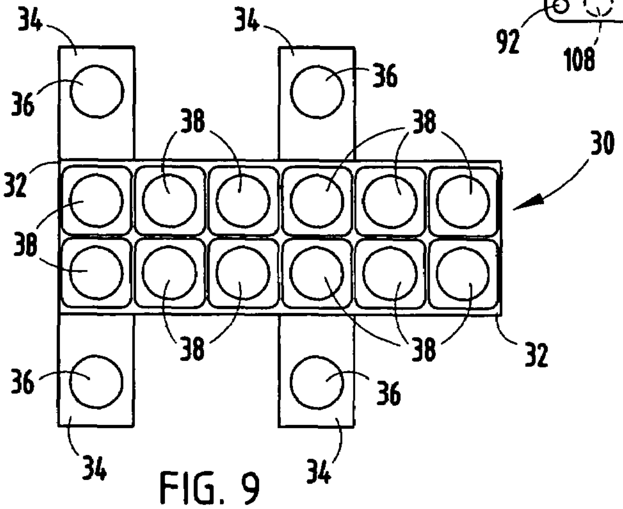
FIGS. 9 and 10 are top plan views of two different printing surfaces of the printer block of the present invention.

Printing surface 32 of printer block 30 can be configured in a variety of specified patterns to create a variety of complementary hydrophobic barriers 120 on examination slide 80. Referring to FIG. 9, when printer block 30 is moved from the first position (FIG. 3) to the second position (FIG. 2), printing surface 32 of printer block 30 is raised above and out of the hydrophobic liquid 20 contained in vessel 12. As printing surface 32 is raised out of hydrophobic liquid 20, excess hydrophobic liquid 20 drains through printer block apertures 38 into the hydrophobic liquid 20 contained in vessel 12, except that sufficient hydrophobic liquid 20 is held on printing surface 32 and covers printing surface 32 in the specified pattern of printing surface 32. Through movement to the second position of printer block 30 (initiated by actuator 40), printer block 30 is brought close enough to the examination slide 80, held in slide holder 22, so that the hydrophobic liquid 20 carried on printing surface 32 is printed on or transferred from printing surface 32 to the top slide surface 88 of the examination slide 80 (FIG. 2). The printing surface 32 of printer block 32 shown in FIG. 9 will place on examination slide 80 a hydrophobic barrier 120 for twelve separate examination wells 122. The specified pattern of printing surface 32, shown in FIG. 10 will create on examination slide 80 a hydrophobic barrier 120 sufficient for eight examination wells 122 to contain and separate eight samples.

The hydrophobic barrier 120 placed on the examination slide 80 using the apparatus and/or method of the present invention preferably is unaffected by the detergents and solvents used in various steps of the microarray protocol, and the height of the hydrophobic barrier 120 does not impede scanning of the examination slide 80 in a microarray scanner. In a more preferred embodiment, the height of hydrophobic barrier 120 is less than 250 micrometers.

The present invention permits multiple assays to be run on a single examination slide with minimal risk of contamination between assays. Specifically, when multiple liquid samples (not shown) are each separately placed in the examination wells 122 of the examination slide 80 for analysis, the hydrophobic barrier 120 prevents leakage or migration of the sample liquid from one examination well 122 to another examination well 122 on the examination slide 80, retaining each sample in a discrete, well-defined area on the examination slide 80 and preventing contamination between the samples. Further, because of the control permitted when using a slide made by the apparatus or method of the present invention, the volume contained by the examination wells 122 can be uniform among the examination wells on an examination slide.

A preferred embodiment of the method of the present invention includes obtaining hydrophobic liquid 20 and placing hydrophobic liquid 20 into vessel 12 of apparatus 10. The method further includes obtaining an examination slide appropriately sized for use in connection with slide holder 22 of apparatus 10. The size of examination slide 80 is well known to one of ordinary skill in the art, having a length, width, and thickness of a conventional microscope slide. An operator places slide rear end 84 of examination slide 80 onto step channel shelves 78 with top surface 88 of slide 80 facing toward printing surface 32 of printing block 30. The examination slide 80 then is slid into slide holder 22 toward rear vessel wall 16 until examination slide rear end 84 is stopped by stop 72 of slide holder 22. So positioned, examination slide 80 rests within slide holder 22 with examination slide front end 82 projecting forwardly from front end 90 of slide holder 22 (FIG. 2). Initially, printer block 30 is in the first position (FIG. 3). Prior to operation of the actuator 40 of the apparatus 10, right vessel cover 24 is removed. In order to place a hydrophobic barrier in a specified pattern onto the examination slide 80 contained within slide holder 22, an operator grasps handle 64 of lever arm 42 and pulls lever arm 42 from its position adjacent rear vessel wall 16 to its position adjacent front vessel wall 14, thereby moving printer block 30 from the first position (FIG. 3) to the second position (FIG. 2), pressing printer block 30 upwardly toward examination slide 80, and laying down a hydrophobic barrier 120 in the pattern specified by printing surface 32. The operator moves lever 42 a sufficient distance to cause the hydrophobic liquid 20 on printing surface 32 to be transferred to top surface 88 of examination slide 80, thereby creating hydrophobic barrier 120 in a specified pattern on the examination slide 80. The operator can control the size (e.g., height) of the hydrophobic barrier 120 placed on the examination slide 80 by contacting for a longer or shorter period of time the hydrophobic liquid 20 carried on printing surface 32 with slide top surface 88. Additionally, hydrophobic barrier size can be controlled by varying the composition of the hydrophobic liquid 20 and the temperature of the hydrophobic liquid 20 contained in vessel 12.

In a preferred embodiment of the present invention, the hydrophobic liquid 20 is a wax composition naturally occurring in a solid phase at room temperature. Accordingly, in this embodiment, the operator activates heater 110 by heater control 112 such that hydrophobic liquid 20 is converted from a solid phase to a liquid phase before the operator initiates actuation of actuator 40. Once the operator has transferred the hydrophobic liquid from the printing surface 32 of the printer block 30 to slide top surface 88 of examination slide 80, the hydrophobic liquid 20 returns to room temperature and cures into a solid phase. The operator then can withdraw the examination slide 80 from slide holder 22. After the examination slide 80 is removed from the slide holder 22, the operator moves lever arm 42 back to its position adjacent rear vessel wall 16, thereby returning printer block 30 to the first position (FIG. 3). After operation of apparatus 10, right vessel cover 24 is replaced on top of vessel 12.

An operator may print DNA or antibody microarrays on examination slide 80 before or after placing a hydrophobic barrier 120 on the examination slide. Frequently, the microarrays are printed on a nitrocellulose pad on top surface 88 of slide 80 (not shown). Further, for example, each array in an examination well could include 96 antibodies specific to proteins of interest, printed in triplicate on the top surface 88 of the examination slide 80. Each examination well 122 could accommodate up to several thousand spots of DNA or antibodies. If DNA or antibodies are printed on the examination slide after placing the hydrophobic barriers on the slide, then the particular apparatus used to print the DNA or antibodies must be considered. Specifically, in a typical apparatus for printing DNA or antibodies on a slide, one or more printer pins are mounted above the examination slide and there is a gap (e.g., 500 micrometers) between the tips of the printer pins and the top surface of the slide. Thus, when DNA or antibodies are printed on the slide after the hydrophobic barriers are placed on the slide, in order to avoid interference with the printer pins of the DNA or antibody printing apparatus, the height of the hydrophobic barrier on the examination plate must be shorter than the gap between the tips of the printer pins and slide top surface.

In one embodiment of the method of the present invention, an operator prints an array (not shown) on top surface 88 of slide 80 and thereafter inserts the examination slide 80 into slide holder 22 with top surface 88 of the examination slide 80 facing downwardly toward printing surface 32 of printer block 30. In this manner, using apparatus 10, the hydrophobic barrier 120 will be placed around the printed arrays, creating a separate examination well for each array. Further, the operator can create examination slides having varying numbers of examination wells, depending upon the specified pattern of the printing surface 32 of printer block 30. For example, the printer block shown in FIG. 9 can be used to create a hydrophobic barrier for a twelve well examination slide, and the printer block shown in FIG. 10 can be used to create a hydrophobic barrier for an eight well slide.

The apparatus and method of the present invention also can be automated or robotic, rather than manual, including apparatus components and method steps to automate any of the following: (a) insertion/removal of the examination slide into the slide holder; (b) moving the printer block carrying hydrophobic liquid on the printing surface toward the examination slide to lay down the hydrophobic barrier in a specified pattern; and (c) simultaneously loading samples into each of the examination wells on an examination slide (e.g., twelve wells on an examination slide would be simultaneously filled with twelve different samples).

An example for using an examination slide made according to the apparatus and method of the present invention includes testing blood serum from cancer patients in which proteins in the serum have been radio labeled. A treatment or control sample "A" and a reference sample "B" are loaded into a single examination well by micropipetting. Because of the hydrophobic barriers on the examination slide, samples from several patients or several treatment conditions can be assayed in adjacent examination wells on a single examination slide with very little risk of contamination between the different samples on the slide. After loading the samples on the examination slide, the examination slide is incubated so the proteins in sample A and the proteins in sample B can competitively bind to the antibodies printed in each examination well on the examination slide. The examination slide is then washed to remove reagents and unbound proteins, and the slide is scanned to detect the relative abundance of proteins in each sample in each examination well.

It will be understood by those who practice the invention and those of ordinary skill in the art that various modifications and improvements may be made to the invention without departing from the spirit of the disclosed concept. The scope of protection afforded is to be determined by the claims and the breadth of interpretation allowed by the law.

The invention claimed is:

1. An apparatus for placing a hydrophobic barrier on an examination slide, the apparatus comprising:

(a) a vessel configured to contain a hydrophobic liquid;

(b) a printer block having a printing surface configured to carry said hydrophobic liquid and configured to form a hydrophobic barrier on said examination slide in a specified pattern, (i) wherein the printer block is movable between a first position in which the printing surface of the printer block is in said hydrophobic liquid in the vessel, and a second position in which the printing surface of the printer block is out of the vessel;

(c) a slide holder for holding said examination slide adjacent the printing surface of the printer block when the printer block is in the second position; and (d) a reversible actuator for moving the printer block between the first position and the second position.

2. The apparatus of claim 1 further comprising a heater for maintaining said hydrophobic liquid in a liquid phase.

3. The apparatus of claim 1 wherein the actuator initiates movement of the printer block from the first position to the second position thereby transferring said hydrophobic liquid from the printing surface of the printer block to said examination slide and forming a hydrophobic barrier on said examination slide in the specified pattern.

4. The apparatus of claim 1 further comprising a guide mechanism to align the printing surface of the printer block with the slide holder.

5. The apparatus of claim 4 wherein the guide mechanism includes at least one guide post and at least one apertured flange on the printer block, the aperture of the flange sized to accommodate the guide post and to enable the printer block to slide on the guide post.

6. The apparatus of claim 1 wherein the actuator includes an axle having an attached lever arm and an attached pivot member.

7. The apparatus of claim 6 wherein the axle is rotationally mounted to a pivot collar.

8. The apparatus of claim 6 wherein the pivot member includes a cammed surface.

9. The apparatus of claim 1 wherein actuator includes a handle.

10. The apparatus of claim 1 wherein the specified pattern forms a hydrophobic barrier defining eight examination wells.

11. The apparatus of claim 1 wherein the specified pattern forms a hydrophobic barrier defining twelve examination wells.

12. The apparatus of claim 1 wherein the printer block further includes at least one printer block aperture formed to allow hydrophobic liquid to pass through the printer block.

13. The apparatus of claim 1 wherein the slide holder includes at least one step channel for aligning said examination slide in the slide holder.

14. A method of making an examination slide having defined sample areas, the method comprising the steps of:

(a) obtaining an examination slide, a hydrophobic liquid, and an apparatus for placing the hydrophobic liquid on the examination slide to define sample areas, wherein the apparatus includes (i) a vessel configured to contain the hydrophobic liquid, (ii) a printer block having a printing surface formed in a specified pattern, wherein the printer block is movable between a first position in which the printing surface of the printer block is in the hydrophobic liquid in the vessel, and a second position in which the printing surface of the printer block is out of the vessel;

(iii) a slide holder for holding the examination slide adjacent the printing surface of the printer block when the printer block is in the second position; and (iv) a reversible actuator for moving the printer block between the first position and the second position;

(b) placing the hydrophobic liquid in the vessel and the printer block in the first position;

(c) placing the examination slide in the slide holder;

(d) engaging the actuator to move the printer block from the first position to the second position, to carry the hydrophobic liquid on the printing surface of the printer block, and to transfer the hydrophobic liquid from the printing surface of the printer block to the examination slide in the specified pattern; and (e) removing the examination slide from the slide holder.

15. The method of claim 14, further comprising the step of engaging the actuator to return the printer block from the second position to the first position.

16. The method of claim 14 wherein the hydrophobic liquid is in a solid phase at room temperature absent the application of heat.

17. The method of claim 16 wherein the apparatus further includes a heater to maintain the hydrophobic liquid in a liquid phase.

18. The method of claim 17 including the further step of applying heat to the vessel.

19. The method of claim 14 wherein the apparatus further includes a guide mechanism to align the printing surface of the printer block with the slide holder.

20. The method of claim 14 wherein the actuator of the apparatus includes an axle having an attached lever arm and an attached pivot member.

21. The method of claim 14 wherein the slide holder of the apparatus includes at least one step channel for aligning the examination slide in the slide holder.

22. The method of claim 21 wherein the step of placing the examination slide in the slide holder includes placing the examination slide in the step channel of the slide holder.

* * * * *

UNITED STATES PATENT AND TRADEMARK OFFICE

CERTIFICATE OF CORRECTION

PATENT NO. : 7,547,424 B2
APPLICATION NO. : 11/228588
DATED : June 16, 2009
INVENTOR(S) : Haab et al.

It is certified that error appears in the above-identified patent and that said Letters Patent is hereby corrected as shown below:

<u>Column 1;</u>
Line 30 delete “a” first occurrence.

<u>Column 1;</u>
Line 45 insert --a-- after --such as--.

Figure 10:
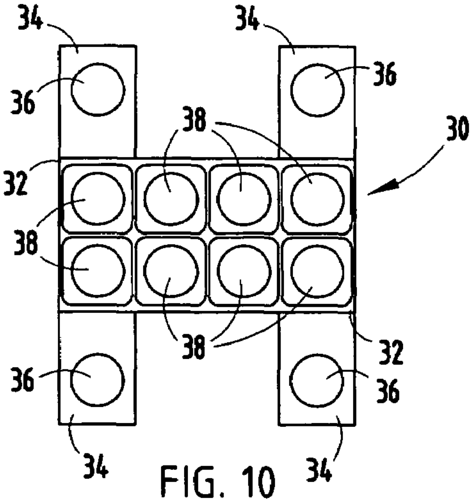
Figure 11:
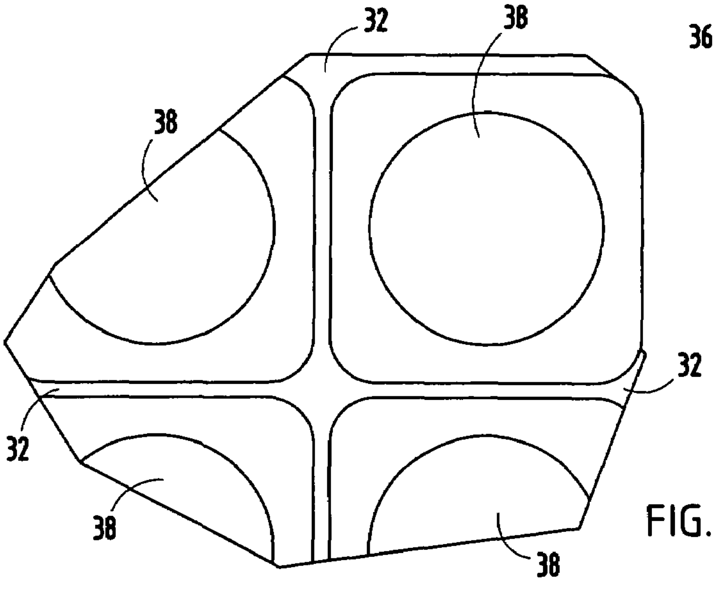
FIG. 11 is an enlarged top plan view of the printer block of FIG. 9 or 10.

<u>Column 3;</u>
Line 16 replace “Fig. 9 or 10” with --Figs. 9 or 10--.

<u>Column 5;</u>
Line 62 replace “printer block 32” with --printer block 30--.

<u>Column 8;</u>
Line 29 replace “movable” with --moveable--.

<u>Column 9;</u>
Line 16 replace “liquid,” with --liquid;--.

<u>Column 9;</u>
Lines 18-19 replace “movable” with --moveable--.

<u>Column 10;</u>
Line 8 replace “Claim 14,” with --Claim 14--.

Signed and Sealed this

Twenty-seventh Day of October, 2009

David J. Kappos
*Director of the United States Patent and Trademark Office*